(12) United States Patent
Valenzuela et al.

(10) Patent No.: US 10,219,063 B1
(45) Date of Patent: Feb. 26, 2019

(54) IN-EAR WIRELESS DEVICE WITH BONE CONDUCTION MIC COMMUNICATION

(71) Applicant: Acouva, Inc., San Francisco, CA (US)

(72) Inventors: Victor Manuel Valenzuela, Hayward, CA (US); Damon Vincent Mercadante, San Francisco, CA (US)

(73) Assignee: Acouva, Inc., San Francisco, CA (US)

( * ) Notice: Subject to any disclaimer, the term of this patent is extended or adjusted under 35 U.S.C. 154(b) by 25 days.

(21) Appl. No.: 15/950,110

(22) Filed: Apr. 10, 2018

(51) Int. Cl.
| | | |
|---|---|---|
| *H04R 1/10* | (2006.01) | |
| *H04R 1/22* | (2006.01) | |
| *H04R 1/08* | (2006.01) | |

(52) U.S. Cl.
CPC ............ *H04R 1/1016* (2013.01); *H04R 1/083* (2013.01); *H04R 1/222* (2013.01); *H04R 2420/07* (2013.01)

(58) Field of Classification Search
CPC ...... H04R 1/1016; H04R 1/083; H04R 1/222; H04R 2420/07
See application file for complete search history.

(56) References Cited

U.S. PATENT DOCUMENTS

| | | | | |
|---|---|---|---|---|
| 2008/0253583 | A1* | 10/2008 | Goldstein | ............ H04R 1/1091 |
| | | | | 381/92 |
| 2009/0010456 | A1* | 1/2009 | Goldstein | .............. H04R 25/02 |
| | | | | 381/110 |
| 2009/0074201 | A1* | 3/2009 | Zhang | .................. H04R 25/407 |
| | | | | 381/92 |
| 2015/0382120 | A1* | 12/2015 | Baskaran | ............. H04R 29/001 |
| | | | | 381/56 |
| 2017/0230752 | A1* | 8/2017 | Dohmen | ................ H04R 5/033 |
| 2017/0347348 | A1* | 11/2017 | Masaki | ............ H04W 72/0406 |

* cited by examiner

*Primary Examiner* — Tuan D Nguyen
(74) *Attorney, Agent, or Firm* — Growth IP; Brian Lao

(57) ABSTRACT

An embodiment of the technology provides a wireless in-ear utility device that rests in the user's ear canal away from the user's eardrum. Embodiments of the in-ear utility device can be configured in a variety of ways, including, but in no way limited to, a multi flexible personal, Streaming Music, and multi internal and external communication device via wireless communication.

19 Claims, 2 Drawing Sheets

IN-EAR WIRELESS DEVICE WITH BONE CONDUCTION MIC COMMUNICATION

CROSS-REFERENCE TO RELATED APPLICATIONS

The present application is related to co-filed U.S. patent application Ser. No. 15/950,122 entitled "Tri-Micro Low Frequency Filter Tri-Ear Bud Tips and Horn Boost With Ratchet Ear Bud Lock," filed 10 Apr. 2018 (U.S. patent application Ser. No. 15/950,122).

TECHNICAL FIELD

Embodiments of the technology relate to systems and methods pertaining to one or more In-Ear Wireless Devices with Bone conduction Mic communication. An embodiment of the technology relates to systems and methods that employ in-ear electronics to provide a wireless in-ear utility device that uses Tri-Ear Buds in the inner ear canal as retention from keeping the In-Ear Wireless Device with Bone conduction Mic from falling out of the user's ears. Embodiments of the technology relate to systems and methods of quick rechargeable interchangeable button cell batteries ranging from 28 mAH/40 mAH/50 mAH/60 mAH/80 mAH/, and/or any other suitable capacity, using a quick rechargeable interchangeable button cell batteries.

BACKGROUND

The following description includes information that may be useful in understanding embodiments of the technology. This description and any descriptions described herein are non-limiting and do not constitute an admission that any of the information provided herein is prior art or relevant to the presently claimed technology, or that any publication specifically or implicitly referenced is prior art.

Ear pieces can be traditionally bulky and uncomfortable, such as through having a large portion of the devices positioned exterior to a user's ear region. Additionally, ear pieces can limited in their technological abilities for battery longevity and connectivity between the right device and the left device communication. Thus, the prospects for exploring new form factors for ear pieces have conventionally been limited.

Similarly, the prospects for exploring new and independent uses (e.g., independent of other user devices such as smartphones) for ear pieces have also been limited conventionally. Therefore, a need exists for more advanced in-ear utility devices that can perform an expanded set of tasks at an improved rate of performance over conventional devices.

OVERVIEW

Embodiments of the technology provide a wireless in-ear utility device comprising a housing with an oval shape trunk to fit into a user's ear canal within the first bend of the ear canal, the housing having a proximal end configured to reside in the user's ear canal (e.g., at a distance no more than 12 to 16 millimeters from the entrance of the user's ear canal). The wireless in-ear utility device can additionally include a microphone port located on an external surface of the device housing and configured to receive external ambient sounds into the wireless in-ear utility device processing system. The wireless in-ear utility device can additionally include a microphone in the housing that receives the external ambient sounds via the microphone port, wherein the received external ambient sounds include sounds representing external sounds in the low/mid/high frequencies (e.g., 50 Hz to 10,000 kHz). The wireless in-ear utility device can also comprise a communications module fitted into the housing and configured for wireless communications, wherein the communication module receives second external sounds from another in-ear utility device located in the user's second ear wherein the second external sounds from the another in-ear utility device include sounds representing all external sounds in the low/mid/high frequencies (e.g., 50 Hz to 10,000 kHz).

The wireless in-ear utility device can additionally include a Bone conduction microphone located in the device housing nearest to the opening of the ear canal and configured to receive resident frequency generated from the inner bone of the jaw/ear canal into the wireless in-ear utility device Bone conduction microphone. In a specific example, the wireless in-ear utility device processing system in conjunction with the bone Mic can be tailored to processing resident frequencies from the low/mid/high frequencies (50 Hz to 10,000 kHz). The wireless in-ear utility device can additionally comprise a communications module fitted into the housing and configured for wireless communications, wherein the communication module receives second in ear bone conduction Mic from another in-ear utility device located in the user's second ear wherein the second internal resident frequencies from the another in-ear utility device include frequencies representing resident frequencies from the low/mid/high frequencies (50 Hz to 10,000 kHz)

The wireless in-ear utility device can additionally include a processing system that calibrates a frequency profile of the user's voice. The wireless in-ear utility device can additionally include a processing system configured to analyze collected data to recognize the user's voice based on resident frequency generated from the inner bone of the jaw/ear canal, where the processing system can be calibrated to match the voice frequency shaping in order to recognizing the user's voice based off the bone conduction Mic.

Embodiments of the technology comprise one or more methods for operating one or more wireless in-ear utility device and/or other suitable devices. Embodiments of the method can include receiving ambient external sounds in a microphone port located at the outer portion of the device housing in-ear utility device, where the housing can include a trunk (e.g., that is oval shape to fit into the user's ear canal within the first bend of the ear canal and having a trunk configured to reside in the user's ear canal at a distance no more than 12 to 16 millimeters from the entrance of the user's ear canal, etc.). The method can additionally comprise receiving ambient external sounds via a microphone port in a microphone located in the device housing, wherein the received ambient external sounds include sounds representing any and all ambient sounds from the low/mid/high frequencies (e.g., 50 Hz to 10,000 kHz). The method additionally comprises receiving second external sounds via a wireless communications module fitted into the housing from another in-ear utility device located in the user's second ear wherein the second external sounds include sounds representing any and all ambient sounds from the low/mid/high frequencies (e.g., 50 Hz to 10,000 kHz). The wireless in-ear utility device includes a processing system that calibrates resident frequency generated from the inner bone of the jaw/ear canal into the Bone conduction microphone, gets post processed through the processing system to shape profile of the user's voice. The wireless in-ear utility device also includes a processing system configured to analyze collected data to recognize the user's voice, such as based on frequencies. In an example, the processing system is calibrated to the user's voice, by having the user's repeat a phrase three times then the frequency is captured, and will only recognize the user's voice.

Embodiments of the technology can additionally include an adapter cable (e.g., with a 2½ and a 3½ millimeter audio jack), that can be snapped-in place of the rechargeable battery. This can allows the users to be able to listen to audio continuously without the need to be battery powered.

The embodiments of the technology comprise a method for operating wireless in-ear utility device. The method comprises receiving ambient external sounds in a microphone port located at the outer portion of the device housing in-ear utility device, these ambient sounds can be sampled by and tuned out or tuned in if the user's chooses a need to listen to certain ambient sounds. Embodiments of the technology can additionally facilitate a hearing impaired to adjust the frequencies they are specifically having difficulty hearing (e.g., to improve upon issues with all frequencies being amplified and causing an hearing impaired to over saturate unwanted frequencies that can further damage their hearing; to improve upon safety issues by amplifying the users frequencies need, etc.).

The embodiments of the technology comprise a method for operating a wireless in-ear utility device. Embodiments of the method can comprise receiving one tap (e.g., and/or another applied gesture, etc.) on the wireless in-ear utility device cap to answer a phone call and two taps (e.g., and/or another applied gesture, etc.) to ignore the phone call. Such features (e.g., for controlling the device through gestures, etc.) can be selectively enabled or disabled (e.g., enabled in loud environments, enabled in environments satisfying a threshold condition, etc.). In an example, in a quiet environment, the wireless in-ear utility device can be configured to accept a voice command that allows the user's to simply say "Answer" to pick up the phone call or to say "Ignore", and the phone call will go to voice mail. Additionally or alternatively, any suitable voice commands can be employed to control functionality of the wireless in-ear utility device. Such functionality and/or other suitable functionality can use an accelerometer in combination with the bone conduction Mic. The accelerometer can measure the position of the user's head at all times (and/or selectively, such as for preserving battery life). Analyses based on accelerometer data can be used for safety and/or driving awareness, and the accelerometer can additionally or alternatively collect data that can be used to measure impact, such as to detect if the user's had an unexpected fall or was in an vehicle accident

BRIEF DESCRIPTION OF THE FIGURES

Figures provided herein may or may not be provided to scale. The relative dimensions or proportions may vary. An embodiment of the technology is sized to fit within an extra small ear canal of a user from the age of 14 and above, without discomfort.

FIG. 1 additionally illustrates an in-ear utility device 102a having a flexible Tri-Ear Buds 101a that covers a portion of the in-ear utility device 102a.

FIG. 3 additionally illustrates the in-ear utility device 300 resting against 302 the inner ear canal, which can allow for the resident frequency to vibrate into in-ear utility device 300, therefore enabling the Bone conduction Mic to pick up the user's voice, such as based off of resident frequency vibrations from the low/mid/high frequency 50 Hz to 10,000 kHz, according to an embodiment of the technology.

FIG. 3 additionally illustrates an embodiment of an in-ear utility device 300 configured to provide enhanced low/mid/high frequencies 50 Hz to 10,000 kHz to allow the user's to adjust the frequencies to enhance their hearing lost on the frequencies they are having a need to boost or suppress certain signals based on loud environments. In quiet environments, the user's can also have the capabilities to enhance the sounds they wish to focus on, according to an embodiment of the technology.

FIG. 3 additionally illustrates an embodiment of an in-ear utility device 300 configured to provide a multi-function communication (hands free) by voice commands or a series of taps, according to an embodiment of the technology.

FIG. 3 additionally illustrates an embodiment of an in-ear utility device 300 configured as a multi, integrated body rather than as one single-pieced body, example 503 is detachable to maintain good ear health and high performance. The battery can also be interchangeable to minimize user downtime, and the Tri-Ear buds 301 are interchangeable, so that the users can choose the right size Tri-Ear buds, and to replace them with a fresh one to maintain good ear health.

DETAILED DESCRIPTION OF EMBODIMENTS OF THE TECHNOLOGY

Embodiments of the technology can include a wireless in-ear utility device comprising an acoustic speaker chamber positioned away from the user's eardrum (e.g., at a distance closer than that of examples of conventional sound-delivery devices but farther than that of examples of medically-regulated hearing aids, etc.). Embodiments of the in-ear utility device may be used for a variety of purposes and can include a variety of electronic packages, such as for use as a hearable device, for use as a Streaming Music wirelessly transmitted and for communication, also can be used as a headphone device, and for use with various external health-monitoring and safety awareness application devices.

Embodiments of the technology provide a wireless in-ear utility device configured to have a variety of electronic packages. The electronic packages may serve a variety of functions, such as connectivity between two in-ear devices, a bone conduction microphone for 100% noise isolation that allows the user to eliminate all external sounds also including all types of wind noise during communication, an external health-monitoring device, and a fitness device, each embodiment having the sensors and electronic configuration needed to carry out its mission. Embodiments of the connectivity between two in-ear utility devices may include an external electronic package that supports the Internet communication, defined as a network of physical objects embedded with electronics, firmware, phone apps, external sensors, and network connectivity, which enables the collection and exchange data between two in-ear utility devices and other devices and/or the user. The existing network infrastructure, allowing more direct integration between the physical phone apps, tablets and computer-based systems by wireless communication.

Figure 3:
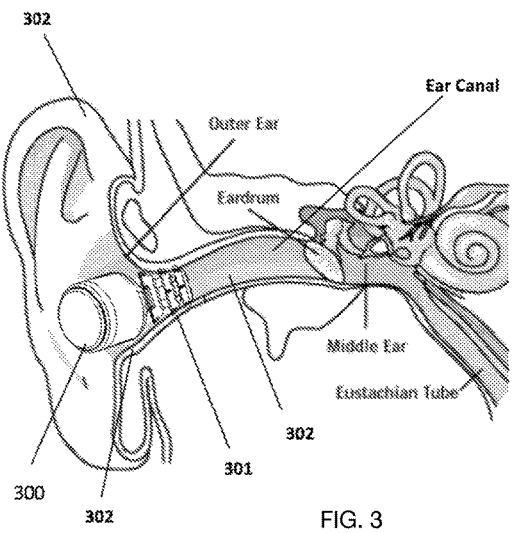
FIG. 3 illustrates the in-ear utility device 300 and the Tri-Ear Buds 301 anchored in 302 by a compression of 10% to 15%, according to an embodiment of the technology.
Figure 4A:
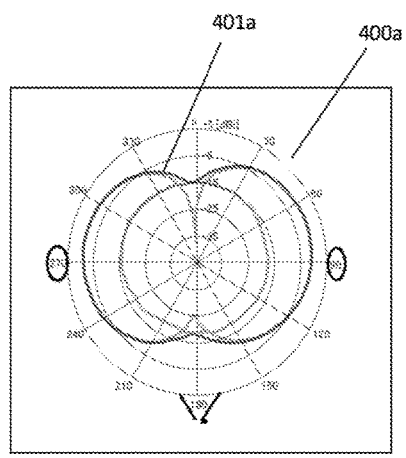
FIG. 4A illustrates the top view of the user's head 400a where (180) is the front and (0) is the rear of the user's head shows a Omni-directional antenna pattern signal, to allow for the in-ear utility device 300 FIG. 3 from the user's right and left ear in-ear utility device to communicate without the user's head blocking the antenna signals from each device.
Figure 4B:
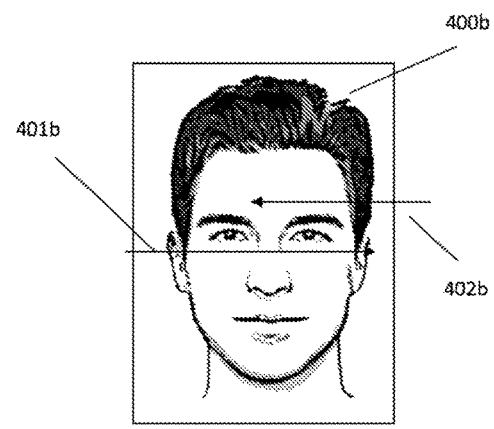
FIG. 4B shows the antenna pattern signal crossing 401b and 402b in front of the user's face 400b, according to an embodiment of the technology.

FIG. 3 illustrates an in-ear utility device 300 inserted into an ear 302, according to an embodiment of the technology. The in-ear utility device 300 includes an electronics package, such as the electronics component package Bone conduction Mic and acoustic speaker chamber. Embodiments of the in-ear utility device 300 may include a disposable Tri-Ear Buds with built in micro filter guard in the body of Tri-Ear Buds 301.

The system (e.g., one or more in-ear utility devices, one or more remote computing systems, etc.) and/or portions of the system can entirely or partially be executed by, hosted on, communicate with, and/or otherwise include: one or more in-ear utility devices, a remote computing system (e.g., a server, at least one networked computing system, stateless, stateful; etc.), a local computing system, a user device, databases (e.g., storing user audio profiles, storing user preferences, etc.), and/or any suitable component. Communication by and/or between any components of the system can include wireless communication (e.g., WiFi, Bluetooth, radiofrequency, etc.), wired communication, and/or any other suitable types of communication.

The components of the system can be physically and/or logically integrated in any manner (e.g., with any suitable distributions of functionality across the components, such as in relation to portions of the method; etc.). However, the system and method can be configured in any suitable manner.

Figure 1:
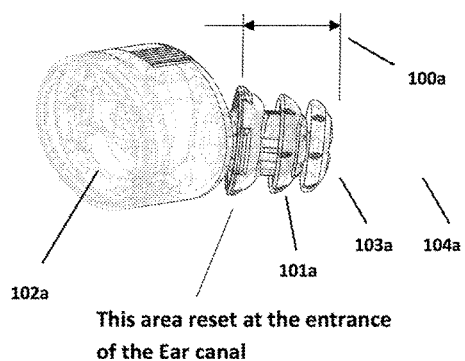
FIG. 1 is a geometrical representation of an example of the in-ear utility device length 100a and indicating penetrating distance from the ear canal entrance FIG. 2b of 201b that is 12 to 16 millimeters, according to an embodiment of the technology.
Figure 2:
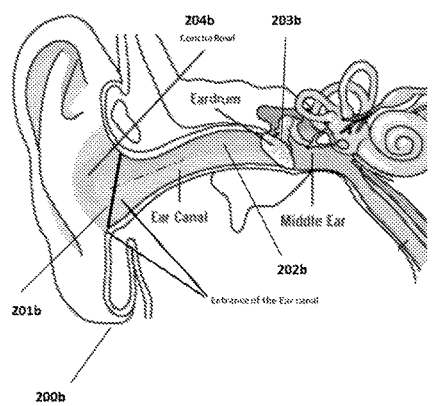
FIG. 2 illustrates a user's ear canal (e.g., the ear canal 202b) that the in-ear utility device 102a is inserted into during normal use, according to an embodiment of the technology.

As shown in FIG. 1a and Fib. 2b, some embodiments of the in-ear device 102a are designed to rest in the ear 2o1b FIG. 2b entrance of the ear canal 12 to 16 mm deep in the canal (e.g., while maintaining a suitable distance from the user's tympanic membrane (eardrum, etc.)). However, the in-ear design can rest in the ear at any suitable depth into the canal, and/or can be positioned at any suitable position relative different regions of the ear. In examples, to satisfy health and safety regulations, the in-ear utility device 102a when placed properly in the ear canal 202b has a proximal tip 103a (along with the speaker 104a) that lies from 12 to 16 mm from the outer edge 201b of the ear canal along a longitudinal axis 104a, according to an embodiment of the technology. Studies have shown that the length of the typical human ear canal 202b varies from 25 mm to 50 mm measured along a curved center axis. Thus, embodiments of the in-ear utility device 102a can reside well away from the eardrum 203b.

The distance of the in-ear utility device 102a to a given user's ear canal 202b varies based on the depth of the user's ear canal 202b. Some users have shallow ear canals while other users have deep ear canals. Therefore, the distance of the in-ear utility device 102a may vary in depth from user to user, but can be configured to reside at any suitable depth in relation to the ear canal and/or other suitable regions of the ear. The in-ear utility device 102a comprises of the longitudinal axis 104a extending on the proximal tip 103a. The distal end of the in-ear utility device 102a can reside just outside the user's ear so that the in-ear utility device 102a may be easily removed by hand and/or other physical means, according to an embodiment of the technology.

FIG. 1a illustrates an embodiment of the technology where components of the in-ear utility device are designed with form factor adapted to the shape of the Concha bowl of the ear 204b, which can function to eliminate one or more pressure points.

The Tri-Ear Buds 101a can facilitate the portion of the device body 102a to rest in the user's Concha bowl 204b. Thus, the body 102a that includes the electronic package can be configured to not touch the user's ear canal 202b. The presence of the Tri-Ear Buds 101a can protect the user against malfunctions of the electronics package. For example, in the event of a short, the user can be protected from shock and heat because of the presence of the Tri-Ear Buds 101a. In examples, the user is protected by the Tri-Ear Buds 101a in part because certain embodiments of the Tri-Ear Buds 101a are constructed from a Bio-compatible medical grade material. Additionally or alternatively, any suitable components of the in-ear utility device can be constructed of Bio-compatible medical grade material, and/or any other suitable adapted for biocompatibility.

The Tri-Ear Buds 101a may also include six to twelve (and/or any suitable number) of channels configured for ear breathability, which can allow the in-ear utility device 102a to be worn comfortably by the user for extended periods of time. The channels can also provide the user with non-occluded aural access to ambient outside sounds in the low frequencies 50 Hz to 300 Hz (and/or of any suitable frequencies), according to an embodiment of the technology.

Thus, portions of the user's ear canal 202b can remain non-occluded by the in-ear utility device 102a due, in part, to the channels. A user of the in-ear utility device 102a can hear sounds external to the in-ear utility device 102a while being shielded from increased pressure in the ear canal 202b due to the presence of the in-ear utility device 102a in the user's ear canal 202b.

The material selection for the in-ear utility device 102a may facilitate the in-ear utility device 102a in entering the ear 202b while facilitating retention 301 of the in-ear utility device 102a in the ear for long periods of time (e.g. while exercising, performing other physical activities, etc.). Embodiments of the technology provide an in-ear utility device 102a covered in (e.g., the Tri-Ear buds 101a) (or composed of) a flexible material that is comfortable to wear for a long period of time and can facilitate retention in the ear canal without a need for additional customization. For example, the Tri-Ear Buds 101a covering the in-ear utility device 102a can possess a shape, form-factor, a material construction, and/or other suitable characteristics that can account for variations in size of user's ear canals (e.g., extra small, small, medium, large and extra-large). In variations, different variants of the tri-ear buds can be constructed to account for physical differences in user's ear regions.

Embodiments of the in-ear utility device 102a may be waterproof and worn in many environments, such as during swimming or while bathing. The in-ear utility device 102a may also be worn during sleep without discomfort. This may allow the in-ear utility device 102a to be utilized during times when conventional sound devices are uncomfortable, do not work, are painful to use, and/or are otherwise unsuitable for such contexts.

However, the tri-ear buds can be configured in any suitable manner.

Electronic Component Package

The electronic component package 102a may include one or more electronic components such as a microphone, a connectivity between both module and Smartphone's, an acoustic speaker chamber, a replaceable rechargeable battery, a DSP/CODEC processing system, a bone conduction voice recognition microphone, a gyro sensor, accelerometer, various external sensors, and/or any other suitable components according to an embodiment of the technology. The in-ear utility device can include any number of electronic component packages, and an electronic component package can include any number of components and/or type of components (e.g., one microphone and one bone conduction Mic, to provide expanded capabilities; any suitable number of microphones and/or sensors; etc.). The individual components in the electronic component package can be integrated with PC board circuitry to provide functionality for such components, such as in a manner known to ordinarily skilled artisans, except when noted herein, etc.)

In examples, the small form factor for the in-ear utility device 102a requires the application of smaller electronic components than the components typically found in other head-mounted devices, such as Classic Bluetooth devices, according to an embodiment of the technology. Additionally or alternatively, the in-ear utility device and/or components thereof can have any suitable form factor, size, and shape. In examples, the circuit connecting the electronic components suggests the application of rigid and flexible PCB circuitry, but any suitable circuity construction can be applied in operating the components of the in-ear utility device. The micro miniature components provide a means for assembling to a miniature substrate PCB, such as where the size of the PCB and/or other suitable components can facilitate keeping the in-ear utility devices comfortable in the users' ears for extended periods of time.

However, the in-ear utility device can include any number of electronic component packages, and electronic component packages can be configured in any suitable manner.

Bone Conduction Microphone and Acoustic Speaker Chamber

The Bone conduction microphone functions to communicate with the acoustic speaker chamber. The bone conduction microphone can pick up low/Mid/High resident frequencies 50 Hz to 10,000 kHz from the inner jaw/ear canal transmitted into the digital signal processing system (DSP), and can subsequently be outputted into the acoustic speaker chamber.

The hearing aid microphone can be a significantly stronger microphone (e.g., such as in relation to the range of detection for sound decibels; such as of a greater strength than typically found in conventional ear devices, etc.). For example, the hearing aid microphone may operate in the range of 20 Hz to 10,000 kHz. In examples, the hearing aid microphone can detect the whole spectrum of human hearing, according to an embodiment of the technology.

Because the microphone can include an increased sensitivity for picking up low/mid/high frequencies compared to similar components found in hearing aids, the in-ear utility device 102a can filter out unwanted noise or tune in sounds that the user wishes to focus on, especially given the microphone of increased power, while noise removal can be accomplished by means of an appropriate hardware configuration and the tuning of the signal processing system DPS.

The microphone does not need to communicate with the speaker, exclusively, or at all in various embodiments of the technology. The microphone may be employed for tasks not directly connected with the speaker and vice versa. Additionally or alternatively, any suitable components of the in-ear utility device 102a can communicate with, be integrated with, operate independently of, and/or be otherwise associated or independent of other components of the in-ear utility device 102a. In an embodiment of the technology, the microphone can take a sample of the noise environment and filter out the unwanted noise, and can sample other user's language and translate it to the owner languages for a two way communication in any language vice versa. Additionally or alternatively, language translation and/or any other suitable modifications to audio input sampled at the microphone can be performed in any suitable manner (e.g., through employing artificial intelligence algorithms and/or other suitable techniques at the processing system, etc.).

Figure 5:
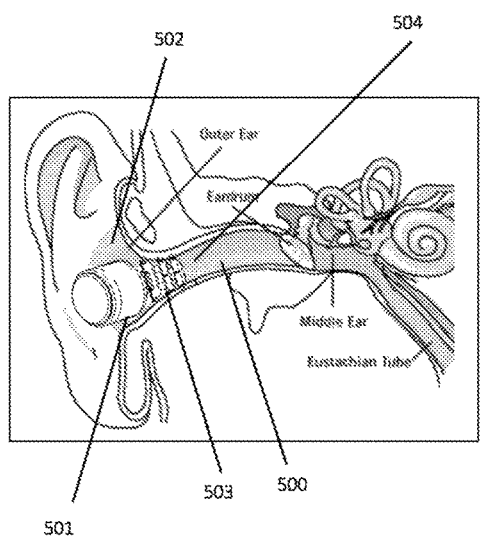
FIG. 5 illustrates an example of the in-ear utility device 501 residing mainly in the Concha bowl 502 (Outer Ear) and does not require any anchoring, the anchoring, the retention 503 Tri-Ear Buds in the ear canal 500 of a compression force of 10% to 15% is applied by 503 against 504 (e.g., which can allow for the user to experience extreme comfort by keeping the compression at 10% to 15% plus or minus 4% compression force, etc.) according to an embodiment of the technology.

The speaker can reside farther away from the user's eardrum (e.g., the eardrum 203b shown in FIG. 2b) than the microphone, but can be positioned relative one or more microphones and/or the user's eardrum in any suitable configuration. As shown in FIG. 5, the speaker 504 port can be disposed at the proximal tip of the body of the in-ear utility device 501 while the microphone is disposed in the distal portion of the in-ear utility device 501. The microphone may be external to the ear and/or otherwise positioned relative the ear region.

In some embodiments, the distance between the acoustic speaker chamber and the microphone are such that the components are isolated from each other, which can lower likelihood of feedback between the microphone and the acoustic speaker chamber. This allows for the acoustic speaker chamber and the microphone to be placed closer together without feedback between the two components, according to an embodiment of the technology.

In embodiments, audio received by an Omni-directional antenna signal to allow wirelessly transmitted Music through the DSP and to the acoustic speaker chamber may come from external wireless communications module, such as when the wireless communications module is configured for Classic Bluetooth® communications 3.0, 4.0 up to 4.1 and up.

In variations, the in-ear utility device can include any suitable number of audio sensors (e.g., any suitable number of microphones) for collecting audio inputs from the environment.

However, the bone conduction microphone(s) and acoustic speaker chamber(s) can be configured in any suitable manner (e.g., for facilitating improved audio collection and playback, etc.).

Processing System and Communication

In some embodiments, the in-ear utility device 501 includes an internal processing system, which can function to process data (e.g., audio inputs collected at microphones), output data (e.g., user identification based on voice, etc.), control components (e.g., control operation of sensors, the acoustic speaker chamber, and/or other suitable components), communicate with other suitable components (e.g., integrate with the electronic component package for sending instructions via the communications module to external wireless devices and/or other suitable devices, such as a remote computing system, etc.).

The internal processing system in the in-ear utility device 501 can access data and/or execute firmware applications, according to an embodiment of the technology. The data and firmware applications can be shared with external communication devices/or delivered to the processing system via the communications with external module that have a remote storage device located away from the in-ear utility device 501. For example, the processing system might execute a firmware application that resides on a mobile phone linked to the in-ear utility device 501. A skilled artisan will appreciate that multiple applications known in the art may be utilized by the processing system. A variety of different data and firmware applications herein have been labeled, as an indication that the data and/or firmware applications are stored in the data storage component and cloud based. In variations, distribution of processing functionality for performing operations described herein can be allocated across the processing system and one or more other suitable components (e.g., external processing systems; remote computing systems; other in-ear utility devices; other user devices such as mobile phones; other in-ear processors of the processing systems, etc.)

In variations, the processing system may be configured to perform operations to distinguish meaningful speech, from bone conduction. Such instructions may perform operations for receiving low frequency signals from the bone conduction microphone, determining whether the sound signals represent meaningful speech, according to various criteria of the voice being calibrated and in the data storage of the processing system, providing signals represent meaningful speech, and filtering the sounds from the DSP processing system to the acoustic speaker chamber. Such instructions for a speech detection program may be present in the data processing system of the in-ear utility device 501 or a coupled external computing device.

The processing system 207 may comprise a DSP/CODEC, or a like computing device, or may alternatively comprise a simple circuit that directs the operations of the various components in the electronic component package, according to an embodiment of the technology.

In some embodiments, the processing system 207 may be a significantly more powerful computing device than conventionally found in hearing aids. For example, the processing system DSP/CODEC are solution with wireless connectivity, includes true noise cancellation through bone conduction Mic. Thus, in some embodiments of the technology, the processing system may include some of the other components. The processing system may require higher power than the typical hearing aid processing system for their wireless communication that is not common in hearing aids, where the power requirements can be satisfied by the batteries and/or other suitable power provision mechanism.

However, the processing system can be configured in any suitable manner.

Wireless Communication Module

In some embodiments of the technology, the in-ear utility device 501 can communicate Omni-directionally via a network. In such embodiments, the wireless communications module 501 may comprise a Classic Bluetooth® digital wireless protocol such that the in-ear utility device 501 may communicate with a remote computing device and/or other suitable components described herein. Classic Bluetooth® technology provides a communication link. The Classic Bluetooth® transceiver in an embodiment of the wireless communications module 501 may be configured to establish a wireless data link with a suitably equipped mobile computing external devices and/or other in-ear utility devices. Additionally or alternatively, any suitable communication mechanism can be used for communication by and/or between any components described herein (e.g., through WiFi, cellular network, other types of Bluetooth, radiofrequency, wired communication, etc.).

The in-ear utility device 501 may also include functionality (e.g., the wireless communication module 501) to communicate Omni-directionally via a long-range wireless network antenna signals. In one embodiment, the long-range wireless network includes a cellular network. In another embodiment, the long-range wireless network includes a multimedia communications network. In another embodiment, the long-range wireless network includes wireless technologies.

The wireless communications module 105 are configured to communicate with a remote server or network. In one embodiment, the remote network cloud platform can communicate with the processor of the in-ear utility device by way of the wireless communication module in order to facilitate operations described herein (e.g., voice recognition, ambient sound detection, controlling sensor operation, storing and/or retrieving user data, data analysis, etc.).

However, the wireless communication module can be configured in any suitable manner.

Sensors and External Sensor Arrays

In embodiments, the in-ear utility device 501 may include one or more sensors configured to detect and/or measure various phenomena (e.g., inputs, stimuli, etc.). In one embodiment, the in-ear utility device 501 operates with one or more external sensors configured to detect a physiological parameter of the user. Physiological external parameters detected or measured by the sensors may include body temperature, pulse, heart rate, VO2 Max (also known as maximal oxygen consumption), pulse oximetry data, respiratory rate, respiratory volume, maximum oxygen consumption, cardiac efficiency, heart rate variability, metabolic rate, blood pressure, EEG data, galvanic skin response data, and/or EKG/ECG. Thus, the sensors may detect, for example, the ambient temperature, humidity, motion, GPS/location, pressure, altitude and blood analysts such as glucose and the sun UV of the user of the in-ear utility device 501. The sensors can be sized to fit within an in-ear utility device and can be configured with power requirements adapted to the characteristics of the in-ear utility device. In a variation, sensor data collected by sensors external to the in-ear utility device can be communicated to a user by way of the in-ear utility device (e.g., through communication of the sensor data and/or analyses derived from the sensor data, from an external user device including the sensors, to the in-ear utility device, etc.).

In variations, sensors of the in-ear utility device, and/or any other suitable sensors associated with the in-ear utility device (e.g., sensors of a user device configured to communicate with an in-ear utility device), can additionally or alternatively include, pressure sensors, temperature sensors, volatile compound sensors, motion sensors (e.g., accelerometers, gyroscopes, magnetometers, etc.), humidity sensors, depth sensors, location sensors (e.g., GPS sensors, etc.), flow sensors, power sensors, and/or any other suitable sensors.

However, sensors of the in-ear utility device and/or any suitable described herein can be configured in any suitable manner.

Voice Recognition and Ambient Sound

The bone conduction microphone can focus on picking up the voice of the user only, while the second microphone can be focused on detecting ambient sound, according to an embodiment of the technology. Additionally or alternatively, audio detection functionality can be distributed across components of the in-ear utility device in any suitable manner.

The voice recognition (e.g., through analysis by the processing system, etc.) is configured to perform operations to distinguish the user's voice from ambient noise. The voice recognition is received by low resident frequencies signals from inner jaw/ear canal, determine whether the frequency represent the user's voice, processed through the DSP processing system when the frequency signals represent meaningful sound, and the sounds are delivered to the acoustic speaker chamber, according to an embodiment of the technology. As an alternative, the in-ear utility device 501 includes a DSP processing system, such as the DSP processing system that has been configured to execute a program that performs operations to distinguish meaningful sound from ambient noise.

However, analyses associated with voice recognition, distinction from ambient noise, and/or other suitable audio analysis can be performed in any suitable manner.

Quick Interchangeable Button Cell Batteries

Embodiments of the technology can include quick interchangeable batteries for the in-ear wireless devices. In an example, the user can place the in-ear wireless devices in a charger case to charge for a minimum of 15 minutes to 3 hours (and/or any suitable amount of time), where operation of the in-ear utility devices can depend on the state of charge (e.g., where users are not able to use their devices till they are fully charged, etc.) In embodiments, the in-ear utility device 501, has a quick interchangeable silver oxide/lithium-ion button cell battery in-ear wireless devices, that requires no downtime the user's snaps off the battery from the in-ear wireless devices and swaps out with a fully charged battery from the charger case that's fully charged, into the in-ear wireless devices, and the users have no downtime. Using this approach can allow the users to use the in-ear utility devices continuously (e.g., 24 hours a day, 7 days a week) and/or in any suitable context (e.g., on the go performing daily activities, etc.), which can aid with provision of a device operable to improve hearing at all times (e.g., which can aid in industries and contexts requiring constant communication), according to an embodiment of the technology.

Figure 6:
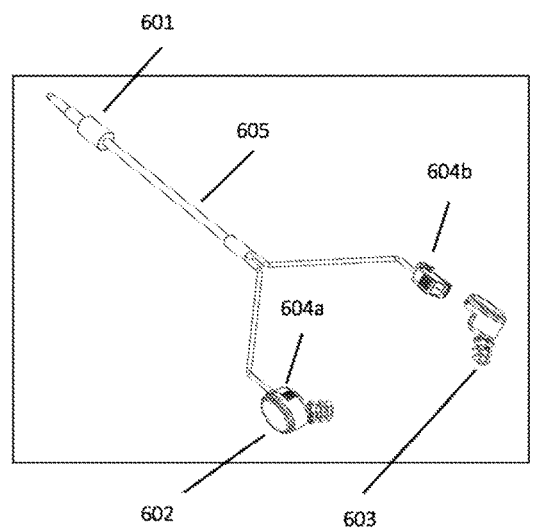
FIG. 6 illustrates the in-ear utility device 602 which includes a cable adapter 605, used to snap in 604a and 604b snap into 602, and the 601 can plug into a 2½ or 3½ audio female jack, according to an embodiment of the technology.

In embodiments, the in-ear utility device 602 in FIG. 6 includes a cable adapter 605, used to snap in 604*a* and 604*b* snap into 602, and the 601 can plug into a 2½ or 3½ audio female jack, example if a user's is on a 12 hour flight and would like to listen to the audio from the TV on the airplane, they can simply plug in the audio adapter into the female audio port from the TV and not have to depend on battery power.

However, the interchangeable button cell batteries, other power provision components, adapters, and/or other related components can be configured in any suitable manner.

Method

Embodiments of a method can include receiving first external ambient sounds at a microphone port located at an outer end of a housing of the in-ear utility device, and at bone conduction Mic configured to focus to the user's voice based on frequency shaping through bone conduction, wherein the housing comprises an oval shaped trunk portion configured to fit into a user's ear canal, wherein the housing further comprises a proximal end configured to reside in the user's ear canal at a distance less than 16 millimeters from the entrance of the user's ear canal; receiving second external ambient sounds via a wireless communications module fitted into the housing, from a second in-ear utility device located in the user's second ear, wherein the second external ambient sounds comprise sounds representing the user's voice; retrieving a voice profile of the user's voice frequency shape from a processing system; and/or recognizing the user's voice based on a post processing of a user frequency profile shape and at least one of the first external ambient sounds and the second external ambient sounds, wherein the user frequency profile shape is associated with the low/mid/high frequencies (50 Hz to 10,000 kHz).

Data described herein (e.g., audio data, voice data, ambient sound data, user profile data, etc.) can be associated with any suitable temporal indicators (e.g., seconds, minutes, hours, days, weeks, etc.) including one or more: temporal indicators indicating when the data was collected, determined, transmitted, received, and/or otherwise processed; temporal indicators providing context to content described by the data; changes in temporal indicators (e.g., data over time; change in data, such as changes in user frequency shape profiles; data patterns; data trends; data extrapolation and/or other prediction; etc.); and/or any other suitable indicators related to time.

Additionally or alternatively, parameters, metrics, inputs, outputs, and/or other suitable data can be associated with value types including: scores (e.g., for the similarity between a calibrated frequency shape profile of the user's voice and a newly determined frequency shape derived from collected audio data, etc.), binary values, classifications (e.g., user identifications; etc.), confidence levels, values along a spectrum, and/or any other suitable types of values. Any suitable types of data described herein can be used as inputs (e.g., for different operations described herein; for portions of the method; etc.), generated as outputs (e.g., of computational models), and/or manipulated in any suitable manner for any suitable components associated with the method and/or system.

One or more instances and/or portions of the method and/or processes described herein can be performed asynchronously (e.g., sequentially), concurrently (e.g., in parallel; concurrently on different threads for parallel computing to improve system processing ability for processing audio data; etc.), in temporal relation to a trigger event (e.g., performance of a portion of the method 100), and/or in any other suitable order at any suitable time and frequency by and/or using one or more instances of the system, components, and/or entities described herein.

Although omitted for conciseness, the embodiments include every combination and permutation of the various system components and the various method processes, including any variations, examples, and specific examples, where the method processes can be performed in any suitable order, sequentially or concurrently using any suitable system components. Any of the variants described herein (e.g., embodiments, variations, examples, specific examples, illustrations, etc.) and/or any portion of the variants described herein can be additionally or alternatively combined, excluded, and/or otherwise applied.

The system and method and embodiments thereof can be embodied and/or implemented at least in part as a machine configured to receive a computer-readable medium storing computer-readable instructions. The instructions are preferably executed by computer-executable components preferably integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the embodiments without departing from the scope defined in the following claims.

We claim:

1. A wireless in-ear utility device, comprising:
a housing comprising an oval shaped trunk configured to reside in a user's ear canal within the first bend of the ear canal, the housing comprising a proximal end configured to reside in the user's ear canal at a distance less than 16 millimeters from the entrance of the user's ear canal;
a microphone port located on an external surface of the housing and configured to receive first ambient external sounds from the low/mid/high frequencies (50 Hz to 10,000 kHz); a microphone located within the housing configured to receive the first ambient external sounds via the microphone port, wherein the received first ambient external sounds comprise sounds from the low/mid/high frequencies (50 Hz to 10,000 kHz);
a bone conduction microphone configured to detect resident frequencies to facilitate user voice recognition; a communications module located within the housing and configured for wireless communications, wherein the communication module receives second ambient external sounds from a second in-ear utility device located in the user's second ear, wherein the second ambient external sounds from the second in-ear utility device comprise sounds from the low/mid/high frequencies (50 Hz to 10,000 kHz);
and a processing system located within the housing, wherein the processing system is configured to identify the user based on a frequency profile shape of the user's voice and at least one of the first ambient external sounds and the second ambient external sounds process the first and the second ambient external sounds based on a frequency profile shape of the user's voice.

2. The wireless in-ear utility device of claim 1, wherein the microphone port, residing at the external surface of the housing, is configured to reside in the user's ear Concha bowl to listen for ambient external sounds from the low/mid/high frequencies (50 Hz to 10,000 kHz).

3. The wireless in-ear utility device of claim 1, wherein the Bone conduction microphone does not include a port, and wherein the Bone conduction microphone is adapted to processing resident frequencies from the low/mid/high frequencies (50 Hz to 10,000 kHz) through a diaphragm, wherein the bone conduction microphone is configured to operate without requiring a fixed distance between the user's mouth and the user's ear canal, and wherein the processing system is configured to calibrate the frequency shape profile of the user's voice based on inputs collected by the Bone conduction microphone.

4. The wireless in-ear utility device of claim 3, wherein the processing system is configured to recognize the user's voice based on matching the frequency shape profile of the user's voice to a frequency profile generated from data associated with the Bone conduction microphone, frequency shape, the processing system is calibrated to match the voice frequency shape in order to recognizing the user's voice.

5. The wireless in-ear utility device of claim 1 further comprising:
a digital signal processing system configured to receive the first ambient external sounds and voice-focused from a bone conduction microphone, and to enhance the first ambient external sounds prior to transmitting the first ambient external sounds to the digital signal processor, wherein the second ambient external sounds from the second in-ear utility device have undergone digital signal processing before transmission to the wireless in-ear utility device, wherein the processing system is configured apply the enhanced ambient external sound and data from an enhanced second internal bone Mic in recognizing resident frequencies from the low/mid/high (50 Hz to 10,000 kHz) frequencies through a diaphragm generated from the inner bone of the jaw/ear canal into the wireless in-ear utility device processing system, for facilitating user voice recognition.

6. The wireless in-ear utility device of claim 1, wherein the Bone Conduction microphone is configured to detect resident frequencies generated in association with the inner bone of the jaw/ear canal.

7. The wireless in-ear utility device of claim 1, further comprising:
an ambient microphone port located at the distal end of the housing and configured to receive external sounds only; and
an ambient focused microphone located in the housing that receives the external sounds via the ambient microphone port,
wherein the processing system is further configured to include the Bone Conduction microphone based on resident frequencies generated from the inner bone of the jaw/ear canal in order to recognizing the user's voice may be configured with an external Mic to execute other process.

8. The wireless in-ear utility device of claim 7 wherein the processing system is configured to improve signal-to-noise ratio based on disabling the ambient focused microphone in response to detecting a phone call, and operating the bone conduction microphone to process, via resident frequencies from the low/mid/high frequencies (50 Hz to 10,000 kHz) through a diaphragm, resident frequencies generated from the inner bone of the jaw/ear canal into the wireless in-ear utility device processing system DSP, wherein the user's voice is heard from the receiving end of a phone or any other communication device.

9. The wireless in-ear utility device of claim 1, further comprising:
an acoustic speaker chamber located within the housing, wherein the processing system is configured to send a digital decoded signal through the acoustic speaker chamber.

10. The wireless in-ear utility device of claim 1 wherein ambient sound through the microphone port is located on outer portion of the housing, wherein the focused on ambient sound through the microphone port is positioned at a location to receive the external sounds.

11. A method for an operating wireless in-ear utility device, comprising:
receiving first external ambient sounds at a microphone port located at an outer end of a housing of the in-ear utility device, and at a bone conduction microphone configured to focus to the user's voice based on frequency shaping through bone conduction, wherein the housing comprises an oval shaped trunk portion configured to fit into a user's ear canal, wherein the housing further comprises a proximal end configured to reside in the user's ear canal at a distance less than 16 millimeters from the entrance of the user's ear canal;

receiving second external ambient sounds via a wireless communications module fitted into the housing, from a second in-ear utility device located in the user's second ear, wherein the second external ambient sounds comprise sounds representing the user's voice;

retrieving a voice profile of the user's voice frequency shape from a processing system; and recognizing the user's voice based on a post processing of a user frequency profile shape and at least one of the first external ambient sounds and the second external ambient sounds, wherein the user frequency profile shape is associated with the low/mid/high frequencies (50 Hz to 10,000 kHz).

12. The method of claim 11, further comprising determining the user frequency profile shape based on prompting the user, through a mobile device application, to provide an audio input.

13. The method of claim 11, wherein the bone conduction microphone is based on resident frequencies generated from the inner bone of the jaw/ear canal and is not dependent on the distance of user's mouth, wherein recognizing the user's voice is based on the resident frequencies generated from the inner bone of the jaw/ear canal in association with the low/mid/high frequencies (50 Hz to 10,000 kHz).

14. The method of claim 11, further comprising:
enhancing the ambient external sounds by a digital signal processing system configured to receive the ambient external sounds from the microphone port and enhance ambient external sounds before sending the ambient external sounds to the processing system.

15. The method of claim 11, further comprising:
improving signal-to-noise ratio associated with the bone conduction Mic and external sounds by the processing system performed through the bone conduction Mic and external sounds outside the region, wherein noise comprising wind and low/mid/high 50 Hz to 10,000 kHz frequencies are cancelled out.

16. The method of claim 11 wherein the bone conduction Mic is a voice-focused microphone, and wherein the bone conduction Mic is not a directional microphone, wherein operation of the bone conduction Mic comprises operation based on resident frequency generated from the inner jaw/ear canal.

17. The method of claim 11, further comprising:
receiving ambient sounds at an ambient microphone port located at the outer side of the housing; and
receiving the ambient sounds in an ambient focused microphone located in the housing via the ambient microphone port,
wherein the processing system is further configured to process external sounds received from the ambient focused microphone.

18. The method of claim 11, further comprising:
playing external sounds by a speaker located near the distal end of the trunk in the housing.

19. The method of claim 11, further comprising:
decreasing power of an electrical signal associated with the acoustic speaker chamber amplified by an internal horn located in the housing device trunk.

* * * * *